United States Patent [19]

Yagi et al.

[11] Patent Number: 4,801,211

[45] Date of Patent: Jan. 31, 1989

[54] HUMIDITY AND DEW POINT DETECTOR

[75] Inventors: Hideaki Yagi; Takahito Kojima; Katsuhiko Horii, all of Aichi, Japan

[73] Assignee: NGK Spark Plug Co., Ltd., Nagoya, Japan

[21] Appl. No.: 918,755

[22] Filed: Oct. 14, 1986

[30] Foreign Application Priority Data

Oct. 12, 1985 [JP] Japan .................................. 60-226017
Oct. 12, 1985 [JP] Japan .................................. 60-226018
Oct. 12, 1985 [JP] Japan .................................. 60-226019

[51] Int. Cl.$^4$ ......................................... G01N 25/02
[52] U.S. Cl. ................................... 374/28; 73/336.5; 338/35; 236/44 E
[58] Field of Search ........................ 73/336.5; 374/28; 338/35; 236/44 E

[56] References Cited

U.S. PATENT DOCUMENTS

| | | | |
|---|---|---|---|
| 3,820,398 | 6/1974 | Rekai .................... | 73/336.5 |
| 4,080,564 | 3/1978 | Nitta et al. ............... | 338/35 |
| 4,208,910 | 6/1980 | Lezius .................... | 73/336.5 |
| 4,335,293 | 6/1982 | Kobayashi et al. ......... | 73/336.5 |
| 4,379,406 | 4/1983 | Bennewitz et al. ......... | 73/336.5 |
| 4,386,336 | 5/1983 | Kinomoto et al. .......... | 73/336.5 |
| 4,419,021 | 12/1983 | Terada et al. ............. | 338/35 |
| 4,419,888 | 12/1983 | Kitamura et al. .......... | 73/336.5 |
| 4,462,930 | 7/1984 | Suzuki et al. ............. | 73/336.5 |
| 4,501,147 | 2/1985 | Niwa ..................... | 73/336.5 |
| 4,594,569 | 6/1986 | Fukushima et al. ........ | 338/35 |

FOREIGN PATENT DOCUMENTS

| | | | |
|---|---|---|---|
| 0079308 | 6/1981 | Japan .................... | 236/44 E |
| 0095539 | 6/1982 | Japan .................... | 236/44 E |
| 0016309 | 1/1983 | Japan .................... | 236/44 E |
| 0146143 | 8/1985 | Japan .................... | 73/336.5 |

*Primary Examiner*—Steven L. Stephan
*Assistant Examiner*—Thomas B. Will
*Attorney, Agent, or Firm*—Sughrue, Mion, Zinn, Macpeak and Seas

[57] ABSTRACT

A humidity detector using a ceramic sensor and a heater to periodically clean the sensor. The output of the sensor is sampled and held while the heater is on. When the detector is turned on, the heater is not started until the sensor has been sampled and held. The timer controlling this operation can be externally reset. When the ceramic sensor is temperature corrected, the humidity output indicates a dew point at a fixed temperature. By adjusting this fixed temperature dew point output according to a sensed temperature, the dew point can be detected.

8 Claims, 8 Drawing Sheets

HUMIDITY AND DEW POINT DETECTOR

BACKGROUND OF THE INVENTION

Field of the Invention

This invention is intended to provide a dew point detector at low cost which is a simple circuit obtained by adding a partial temperature correcting circuit to a humidity detecting circuit and which can detect dew points, the detection of which is difficult even with microcomputers.

This invention also relates to a humidity detector having a heat cleaning function, which has a timer circuit which performs the heat cleaning function and an output holding function after a humidity measuring operation has been carried out for longer than one second.

This invention further relates to a humidity detector with a timer circuit for controlling the hot cleaning operation, in which an output holding operation at the time of start and an automatic cleaning operation are in succession carried out. An optional cleaning operation is performed by connecting an external power source to the timer circuit at a desired time.

The dew point detector of the invention can be effectively employed for general air conditioning systems, air conditioning systems for plants, or dew point control in the field of biotechnology and chemical industry, agricultural vinyl houses, and warehouses.

Background of the Invention

A lithium chloride dew point sensor is advantageous in that it can provide outputs directly without using an intricate circuit.

However, the lithium chloride dew point sensor is disadvantageous in that, as it uses a lithium chloride solution, the lithium chloride is effused if the sensor is becomes wet with dew. In addition, the lithium chloride dew point sensor is not durable in an acid or alkaline atmosphere or a solvent atmosphere. Therefore, it requires routine maintenance, and it is rather troublesome to handle the lithium chloride dew point sensor. In order to eliminate this difficulty, it has been proposed in the art to utilize a semiconductor humidity sensor such as a ceramic humidity sensor combined with temperature sensor in order to detect a dew point. Generally, dew points are calculated from a saturated steam pressure table (JIS Z8806). On the other hand, dew points can be calculated with high-order approximate expressions or recalled from a saturated steam pressure table stored in a microcomputer if an analog-to-digital converter, which is considerably high in accuracy, is used for the measured temperature and humidity. However, an apparatus for practicing the method is necessarily large-scale and is therefore high in manufacturing cost.

A non-heating type humidity sensor becomes inoperable when contaminated for a long period of time. Therefore, when it is required to perform humidity control with high accuracy and high reliability, it is essential to use a heating type humidity sensor which cleans itself. A humidity detecting circuit which utilizes a conventional heating type humidity sensor cannot detect humidity during heat cleaning. Therefore, where it is used for humidity control, during the heat cleaning operation, the output provided before the heat cleaning operation is sampled and held during the cleaning operation. The held output is provided as a false output for ten (10) minutes which is the sum of one (1) minute for the heat cleaning operation and nine (9) minutes for cooling down the humidity sensor.

Furthermore, in the conventional humidity detecting circuit, in order to maintain a high accuracy of the sensor an internal timer is provided, so that simultaneous with turning on the power switch, the cleaning circuit is energized. The cleaning operation is then automatically effected in a predetermined period of the time. Beginning with the second cleaning operation, the output provided immediately before the cleaning operation is sampled and held and the held value continues to be outputted.

If, while the conventional humidity detector is measuring humidity after the first cleaning operation, the electric supply is stopped even momentarily, when electric power is again supplied, the heat cleaning circuit is energized at the same time, and therefore an output different from the real one is provided. That is, in this case, the system employing such a system the humidity detector suffers from abnormal control for ten minutes.

If the power switch is turned off during the next cleaning operation, accurate humidity measurement cannot be made without waiting for ten minutes after the power switch is turned on, even if the sensor is clean.

Furthermore, in the case where the humidity detecting circuit is used as a controllable circuit, a timer circuit is coupled to a ceramic humidity sensor, so that a heat cleaning operation is carried out every predetermined period of time, such as for instance, twenty-four hours. According to one aspect of the invention to be described later, during the heat cleaning operation and the following cooling period the humidity detected before the cleaning operation is held outputted, whereby the measurement is stably and accurately performed at all times.

Even this improved humidity detector is disadvantageous in that, in the case where an atmosphere under test is unfavorable or very much contaminated, the frequency of the cleaning operation carried out every twenty-four hours is not high enough. Therefore the result of measurement is low in accuracy.

Furthermore, when the humidity measuring system intends to perform the cleaning operation with a period shorter than twenty-four hours, it is necessary to switch the power switch for every cleaning operation. Otherwise the cleaning operation is not synchronized with the humidity measuring system. Accordingly, the cleaning operation is effected in twenty-four hours irrespective of the period, and each time the cleaning operation is carried out the humidity detecting operation is suspended, i.e., the measurement cannot be performed.

SUMMARY OF THE INVENTION

An object of this invention is to eliminate the above-described difficulties accompanying a conventional dew point sensor.

More specifically, an object of the invention is to provide a dew point detector in which a general analog type humidity detecting circuit is combined with a simple temperature correcting circuit so that the detection result is accurate over wide temperature and humidity ranges.

The foregoing objects of the invention has been achieved by a humidity detecting circuit including a humidity sensor having a temperature correcting element, an AC-DC conversion amplifier connected to the output terminal of the humidity sensor, and a non-linear amplifier circuit connected to the output terminal of the AC-DC conversion amplifier. A temperature correcting arithmetic circuit is connected to the output terminal of the humidity detecting circuit, so that the nonlinear amplifier circuit in the humidity correcting circuit corrects the relation between relative humidity and dew point, and the resultant dew point value is subjected to temperature correction.

According to another aspect of the invention, the ceramic humidity sensor has a heat cleaning ceramic heater. The heater is provided with a heater controlling timer circuit, and a sample and hold circuit is connected to the output terminal of the detector. The timer circuit is connected to the sample and hold circuit so that, after a humidity measuring operation is performed for longer than one second at the start, a heat cleaning operation and an output holding (sample and hold) operation are together performed every twenty-four hours.

In the humidity detector of the invention, the timer circuit is so designed that, when the power switch is turned on, the cleaning heater is started with a delay time of more than one second owing to the timer circuit. That is, the humidity detecting circuit is operated first, and after the output of the humidity detecting circuit is applied to an output holding circuit, the cleaning circuit is activated, so that the output is held outputted. Thereby the above-described difficulties accompanying a conventional humidity detector are eliminated.

According to a third aspect of the invention, the timer additionally has an external input terminal which is utilized to activate a heat cleaning operation by using an external input at a desired time. As a result, the output holding operation at the start of the detector and an automatic cleaning operation are in succession carried out. Also, an optional cleaning operation is performed with an external input applied to the timer circuit at any desired time.

BRIEF DESCRIPTION OF THE DRAWINGS

Traces (A) through (G) of FIG. 14 are time charts showing the wave forms of signals in the circuit of FIG. 12 or 13.

DETAILED DESCRIPTION OF THE PREFERRED EMBODIMENTS

The construction and operation of a dew point detector according to this invention will be described with reference to the accompanying drawings.

Figure 1:
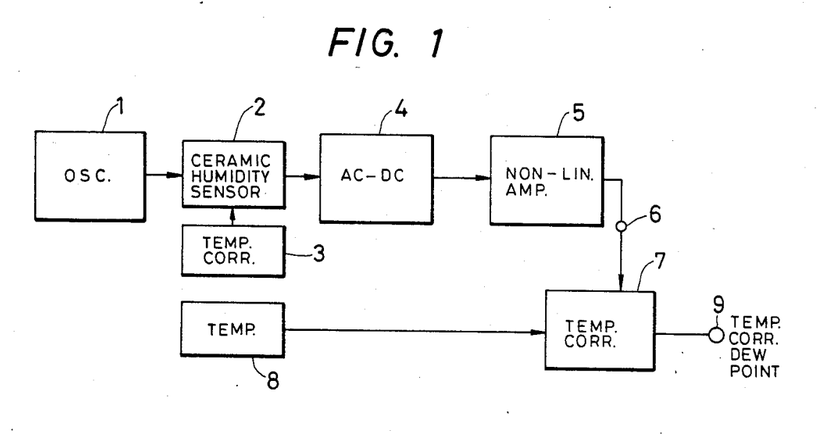
FIG. 1 is a block diagram showing the arrangement of a dew point detector according to the first aspect of this invention.

FIG. 1 is a block diagram of the dew point detector according to the invention. In FIG. 1, A oscillator 1 is a power source for humidity sensors. A ceramic humidity sensor 2 is powered by the oscillator 1. A temperature correcting element 3 is connected to the ceramic humidity sensor 2. An AC-DC conversion circuit 4 is connected to the output terminal of the humidity sensor 2. A non-linear amplifier circuit 5 is connected to the output terminal of the AC-DC conversion circuit 4. An output terminal 6 indicates a dew point at a predetermined temperature (for instance 20° C.). A temperature correcting arithmetic circuit 7 is connected to the dew point output terminal 6. A temperature sensor 8 is connected to an input terminal of the temperature correcting arithmetic circuit 7. An output terminal 9 indicates a dew point value which is obtained by subjecting to temperature correction the dew point output 6 provided at the predetermined temperature.

The part of the above-described circuit of FIG. 1, including the output terminal 6, in which the relative temperature variation of the resistance of the humidity sensor 2 is employed as the dew point output at the predetermined temperature is a humidity detecting circuit utilizing the ceramic humidity sensor 2.

In the dew point detector of the invention, the ceramic humidity sensor is made of metal oxide ceramic material because this type of sensor is thermally stable. Therefore, the ceramic humidity sensor is high in durability, wide in the range of measurement, has a low manufacturing cost and is highly reliable. Furthermore, it can readily provide electrical signals.

As for the metal oxide ceramic humidity sensor, a humidity sensitive element made of a porous sintered body essentially containing $Al_2O_3$, and a humidity sensitive element made of a porous sintered body of $TiO_2$ and $SnO_2$ are known in the art. The principle of humidity measurement is based on the humidity sensitive resistor which utilizes the surfaces of the fine crystals of metal oxide porous sintered material for moisture detection that is, it utilizes the fact that when water molecules corresponding to the amount of vapor in the atmosphere are physically stuck onto or removed from the surfaces of the fine crystals through the porous sintered material, the electrical resistance in the bulk direction of the ceramic changes exponentially. If, in this case, the ceramic humidity sensor is contaminated very much under severe operating conditions, then it can be cleaned by heating it with a ceramic heater (at about 500° C. for one minute). That is, the ceramic humidity sensor can be cleaned automatically at all times to perform measurement with high accuracy.

Figure 6:
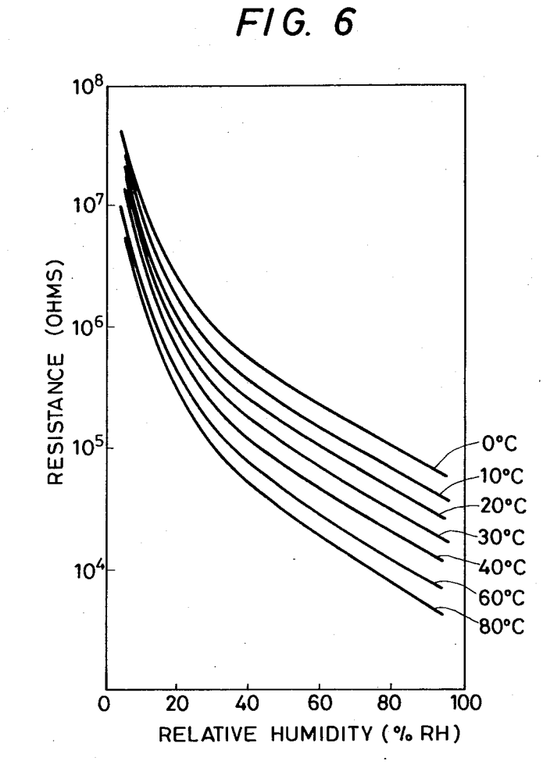
FIG. 6 is a characteristic diagram indicating the temperature dependency of the humidity sensitive characteristic of a ceramic humidity sensor.

A ceramic humidity sensor of this type has a considerably high response characteristic and permits water molecules to quickly stick onto or be removed from the fine crystal surfaces. Therefore, it can measure the humidity of an atmosphere under test within twenty (20) seconds. The sensor resistance decreases exponentially with increasing relative humidity. But the humidity-resistance characteristic of the ceramic humidity sensor depends on temperature. That is, the resistance changes with temperature. Therefore, it is necessary to provide a temperature correcting element 3 such as a temperature compensating thermistor for the ceramic humidity sensor 2 in order to increase the humidity measurement accuracy. The temperature dependence of the humidity sensitive characteristic of the ceramic humidity sensor 2 is as indicated in FIG. 6.

Because of the above-described reason, the temperature correcting element 3 such as a thermistor is provided for the humidity sensor 2 in FIG. 1 to improve the measurement accuracy.

That is, in the humidity detecting circuit of the invention, the measurement value which is obtained by correcting the error attributed to the temperature dependability of the ceramic humidity sensor is subjected to AC-DC conversion in the AC-DC conversion circuit 4. The output of the AC-DC conversion circuit 4 is applied to the non-linear amplifier circuit 5, to directly obtain a linear output, to thereby obtain a dew point value at a predetermined temperature (20° C. for instance).

On the other hand, the relation between dew point and relative humidity is of an intricate function of at least second order. However, the variations of dew point with temperature are seen to be displaced in parallel with respect to temperature variation, and are linear. That is, the variation of dew point with temperature is a linear function.

Figure 5:
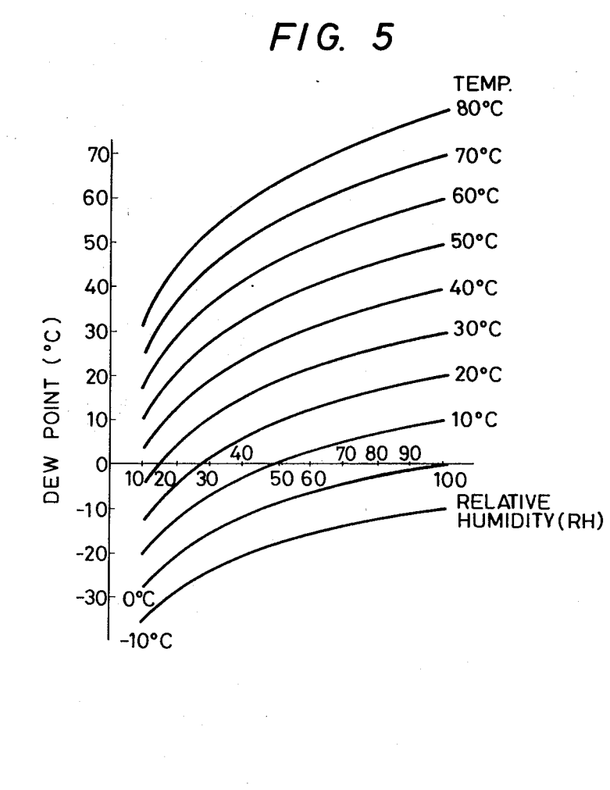
FIG. 5 is a graphical representation indicating the relation between relative humidity and dew point.

Based on the above-described fact, in the nonlinear amplifier circuit 5, the output curve is so adjusted as to coincide with the relation between dew point and the relative humidity described above, thereby to cause the temperature-corrected humidity output described above to meet the characteristic curve of dew point and relative humidity. That is, the temperature correcting arithmetic circuit 3 condenses all the curves of FIG. 6 into a single, temperature independent curve. The non-linear circuit 5 first, however, removes the predominately exponential character of these curves. The scale factors of the temperature correction arithmetic circuitry are such that the input resistance is linearized to the dew point of the 20° C. curve of FIG. 5. As the two curves are made to coincide in this manner, the operation of converting a relative temperature into a dew point by the computer can be eliminated. The dew point output provided at the output terminal 6 in this manner is for a predetermined temperature in FIG. 5 (for example, the curve of 20° C. in FIG. 5). The various temperature curves can be expressed by subjecting the dew point output to temperature correction in the temperature correcting circuit 7 according to the temperature lead by the temperature sensor 8. The dew point output temperature corrected as required is provided at the terminal 9. This operation provides an accurate temperature-corrected dew point output even if the relative humidity changes or the temperature changes. This error-correction operation attributes to the coincidence of the characteristic curved of dew point and relative humidity with the humidity output curve and to the temperature correction accuracy.

Figure 2:
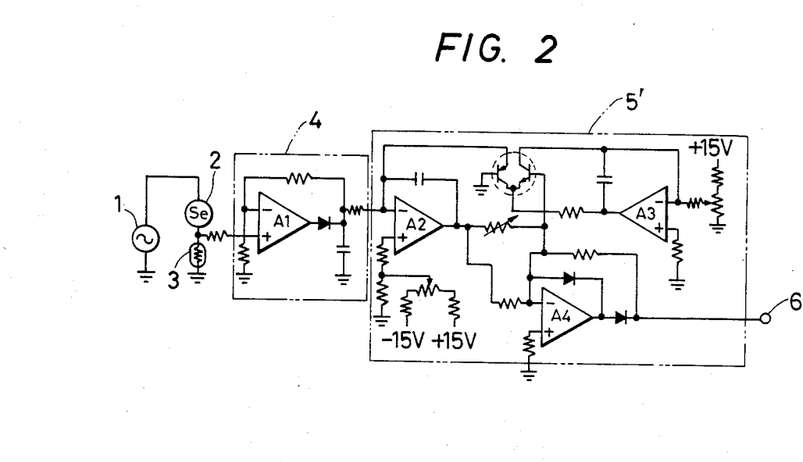
FIG. 2 is a circuit diagram showing one example of a part of the dew point detector of FIG. 1 in which a logarithmic amplifier circuit is employed as its nonlinear amplifier circuit.
Figure 3:
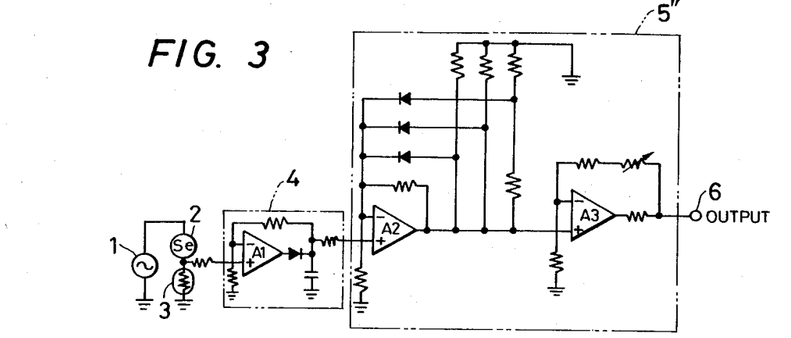
FIG. 3 is a circuit diagram showing another example of the same part of the dew point detector of FIG. 1 in which a polygonal approximation circuit is employed as its non-linearamplifier circuit.
Figure 4:
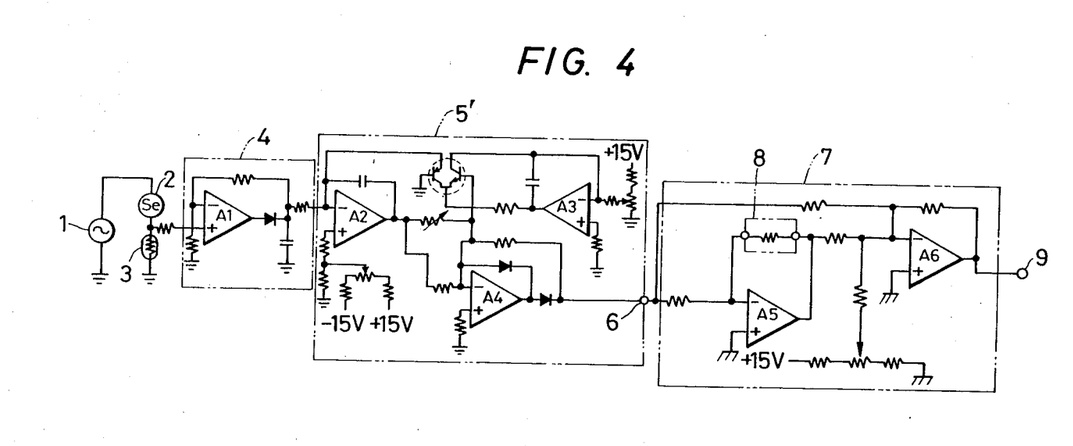
FIG. 4 is a circuit diagram showing the dew point detector in more detail.

A logarithmic amplifier circuit 5' as shown in FIG. 2 or a polygonal approximation circuit 5" as shown in FIG. 3 is employed as the non-linear amplifier circuit in the dew point detector according to the invention. In this case, merely by making the relation curve of relative humidity and dew point coincide with the humidity output curve, the step of storing of the approximated expression in the computer can be eliminated. Nonetheless, the conversion value can be obtained with high accuracy FIG. 4 shows one example of the dew point detector in more detail. In the dew point detector of FIG. 4, the logarithmic amplifier circuit 5' is employed as the non-linear amplifier circuit A temperature correcting circuit 7 is connected to the output terminal of the logarithmic amplifier. This circuit 7 is a linear circuit which simply displaces the curves of FIG. 5 according to the temperature. As a result, the variation in resistance of the humidity sensor which attributes to relative humidity variation is first converted into a dew point at a predetermined temperature and then subjected to temperature correction, to thereby obtain an accurate dew point.

The dew point detector of the invention employs the simple method of forming the relational curve of relative humidity and dew point with the nonlinear amplifier circuit and then adjusting for temperature. However, it can perform the conversion of relative humidity and dew point without storing considerably high order approximation expressions in the microcomputer, for instance, by storing a table of saturated steam pressure as a function of temperature and then reading temperatures. Therefore, a very compact, error-free dew point detector can be provided according to the invention.

An essential feature of the dew point detector resides in that a temperature-corrected humidity input is subjected to non-linear amplification, thereby to obtain a dew point output at a predetermined temperature.

If, in the case where a dew point is detected through conversion by a general relative humidity detector, it is required to process the conversion error with a microcomputer, an analog-to-digital conversion error and an arithmetic error must be taken into account. On the other hand, in the dew point detector simple in circuit arrangement according to the invention, the conversion error is defined only by coinciding the output curve with the reference curve through adjustment of the non-linear amplifier circuit. That is, a specific feature of the dew point detector resides in that the error is extremely small.

Errors (° C. DP) between output values of the dew point detecting circuit according to the invention in which the fixed resistor false inputs of the humidity sensor and the temperature sensor and theoretical values are as indicated in the following Table 1:

TABLE 1

| | | \multicolumn{10}{c}{Dew Point Arithmetic Error (°C. DP)} |
| | | Relative temperature (% RH) | | | | | | | | | |
| | | 10 | 20 | 30 | 40 | 50 | 60 | 70 | 80 | 90 | 100 |
|---|---|---|---|---|---|---|---|---|---|---|---|
| Temper- | −10 | 1.3 | 0.4 | 0.3 | 0.3 | 0.2 | 0.2 | 0.1 | 0.1 | 0.0 | 0.0 |
| ature | 0 | 1.0 | 0.2 | 0.1 | 0.1 | 0.1 | 0.0 | 0.1 | 0.0 | 0.0 | 0.0 |
| (°C.) | 10 | 0.9 | 0.0 | 0.0 | 0.0 | 0.0 | 0.0 | 0.0 | 0.0 | 0.0 | 0.0 |
| | 20 | 0.7 | −0.1 | −0.1 | −0.1 | −0.1 | 0.0 | 0.0 | 0.0 | 0.0 | 0.0 |
| | 30 | 0.7 | −0.1 | −0.1 | −0.1 | 0.0 | 0.0 | 0.0 | 0.0 | −0.1 | −0.1 |
| | 40 | 0.7 | −0.1 | −0.1 | −0.1 | −0.1 | 0.0 | 0.0 | 0.0 | 0.0 | −0.1 |
| | 50 | 0.8 | 0.0 | 0.0 | 0.0 | 0.0 | 0.0 | 0.0 | 0.0 | −0.1 | −0.1 |
| | 60 | 1.0 | 0.2 | 0.1 | 0.1 | 0.1 | 0.1 | 0.1 | 0.0 | 0.0 | −0.1 |
| | 70 | 1.4 | 0.4 | 0.3 | 0.3 | 0.2 | 0.3 | 0.1 | 0.1 | −0.1 | −0.2 |
| | 80 | 1.7 | 0.7 | 0.5 | 0.5 | 0.4 | 0.3 | 0.3 | 0.1 | 0.0 | −0.2 |

As is apparent from Table 1 above, the errors provided by the dew point detector of the invention can be substantially regarded as zero although the detector is simple in circuit arrangement, as was described above. In the case where a humidity sensor requiring no temperature correction is employed, the errors can be minimized by adjusting the non-linear amplifier and adding the temperature correcting circuit.

The dew point detector according to this aspect of the invention is the compact simple circuit obtained merely by adjusting the non-linear circuit of the humidity detecting circuit so that the output curve coincides with the relation curve of dew point and relative humidity, and by adding the simple temperature correcting circuit. Therefore, the dew point detector provided by the invention has a low error similar to that in a data processing operation by a microcomputer. Thus, the dew point detector of the invention should be highly appreciated in practical use.

Figure 7:
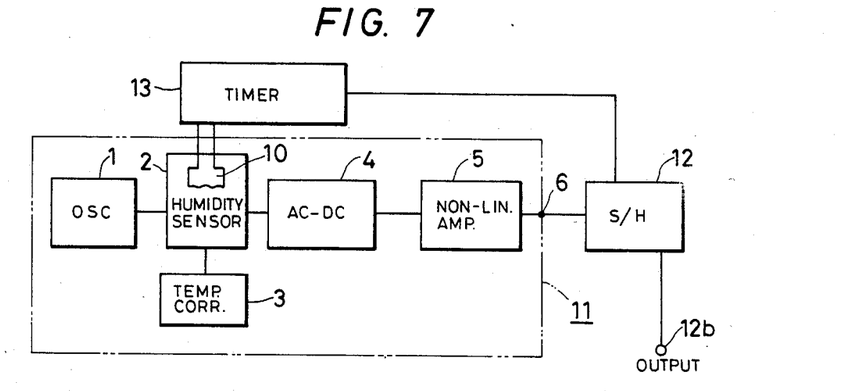
FIG. 7 is a block diagram showing the arrangement of a humidity detector according to the second aspect of this invention.

A humidity detector which has improved hot cleaning properties is shown in FIG. 7. This humidity sensor has many similarities to the dew point detector of FIG. 1. The ceramic humidity sensor 2 has attached thereto a ceramic heater 10. The oscillator 1, humidity sensor 2 and its heater 10, the temperature correction circuit 3, the AC-DC conversion circuit 4 and the nonlinear amplifier 7 constitute a humidity detecting circuit 11. The output terminal of the humidity detecting circuit 11 is connected to an output holding (sample and hold) circuit 12. The sample and hold circuit 12 is connected to a timer circuit 13 provided for the ceramic heater 10. As a result, when the humidity detecting circuit 11 provides an output at the output terminal for the first time after the power switch has been turned on, the output is held by the sample and hold circuit 12 for about ten minutes. During this period (ten minutes) the ceramic heater 10 is initially energized for about one minute to perform the self-cleaning.

Figure 8:
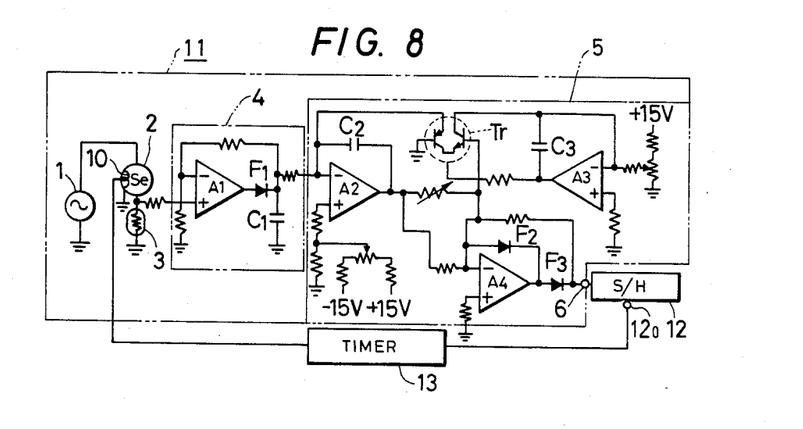
FIG. 8 is a circuit diagram showing the humidity detector of FIG. 7 in more detail.

FIG. 8 shows a specific example of the humidity detector in which a thermistor 3 is employed as the temperature correcting element of the ceramic humidity sensor 2, and a logarithmic amplifier circuit is used as the non-linear amplifier circuit 7. An oscillator 1 which is an AC power source is connected to the ceramic humidity sensor 2. A constant voltage is applied to the series circuit of the variable resistance of the humidity sensor 2 and the thermistor 3. The divided voltage is amplified and rectified by the AC-DC conversion circuit 4 so as to obtain a DC output. The DC output thus obtained is applied to the logarithmic amplifier circuit 7 to obtain a linear output. For this purpose, the DC output is subjected to logarithmic amplification by amplifiers $A_1$ and $A_3$ and a pair of transistors Tr in the logarithmic amplifier circuit 7 to linearize the output, to thereby obtain an output voltage of 10 mV/% RH (relative humidity).

Figure 9:
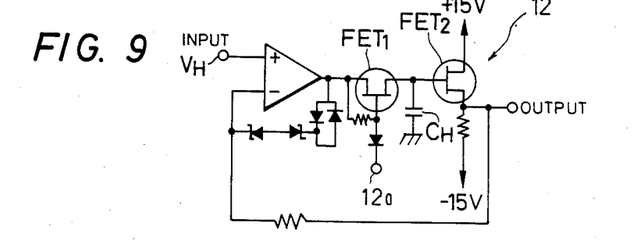
FIG. 9 is a circuit diagram of a sample and hold circuit.

The sample and hold circuit 12 is shown in FIG. 9 in more detail. The voltage output 6 is applied to the terminal $V_H$, and is charged in a capacitor $C_H$ during measurement. When the start signal is applied to a terminal 12a simultaneously when the heat cleaning operation is effected, a transistor $FET_1$ shows a substantially infinite resistance, so that the terminal $V_H$ is disconnected from the capacitor $C_H$. The amount of charging the capacitor $C_H$ is discharged for about ten minutes. On the other hand, the resistance of a transistor $FET_2$ is also substantially infinite, and therefore the amount of charge in the capacitor $C_H$ is maintained unchanged with a holding time of the order of ten minutes.

In the humidity detector of the invention, the sample and hold circuit 12 is connected to the output terminal of the humidity detecting circuit 11 so that the output can be held. The sample and hold circuit 12 is connected to the ceramic heater 10 provided for the humidity sensor 2. At least one to five seconds after the humidity detecting circuit 11 starts its operation, the heater 10 is operated for about one minute to burn or volatize smudges on the surface of the ceramic humidity sensor 2. The output holding operation of the sample and hold circuit 12 is continued for about ten minutes including nine minutes required for cooling the humidity sensor 2. Thereafter, the output holding operation is suspended, and the output of the humidity detecting circuit 7 is delivered out in real time.

Figure 10:
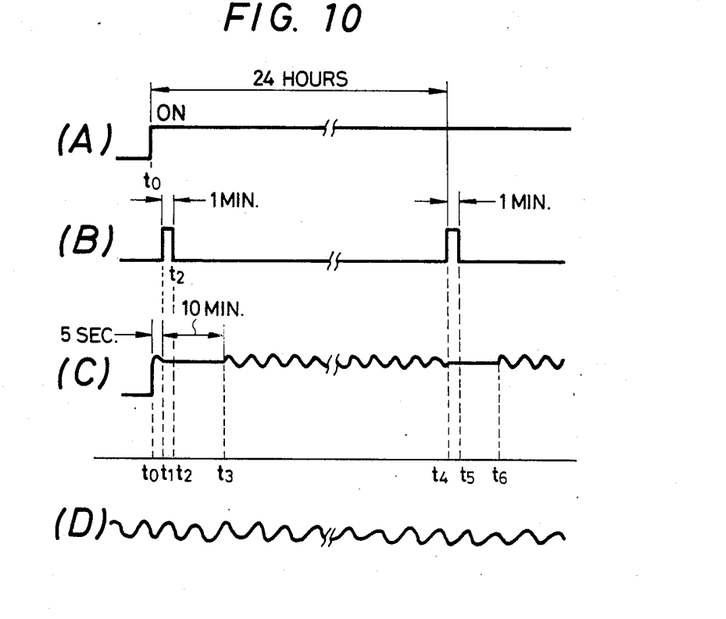
FIG. 10 is a time chart for a description of the operation of a humidity detecting circuit in the humidity detector of FIGS. 7 and 8.

The above-described operations will become more apparent from timing traces (A) through (D) of FIG. 10. That is, as shown in the trace (A) of FIG. 10, when the power switch is turned on at the time instant $t_0$, the output is immediately provided at the humidity output terminal 12 for a period of time $t_0$–$t_1$ (five seconds in trace (C)). The heater 10 is then energized at the time instant $t_1$ to heat the humidity sensor 2 for about one minute to burn or volatize any smudges, etc. thereon (trace (B) of FIG. 10).

When the one minute has passed, the heater 10 is deenergized. When the temperature of the ceramic humidity sensor 2 is changed by heating, the detection value includes corresponding error as much. Accordingly, it is necessary to wait for the ceramic humidity sensor 2 to cool down to the initial temperature. The circuit is so designed that the output is held by the sample and circuit 12 for that period of time ($t_1$ to $t_3$) (trace (C) of FIG. 10).

Therefore, after the time instant $t_3$, the temperature of the humidity sensor 2 is normal, and the humidity measurement is repeatedly carried out with a predetermined period. The above described operation is performed again twenty-four hours thereafter. That is, the heat energization and the output holding operation are repeated as indicated in the trace (B) and (C) of FIG. 3. Trace (D) of FIG. 10 is a time chart showing the wave form of the humidity output 6.

In the humidity detector of the invention, when the power switch is tuned on, the humidity detecting circuit is operated for more than one second irrespective of whether or not the humidity sensor 2 needs to be cleaned. Thereafter the output of the humidity detecting circuit 11 is held, and the cleaning operation is started. The humidity sensor 2 is held for a predetermined period of time (about nine minutes) from the deenergization of the heater. That is, the output is held for about ten minutes until the humidity sensor 2 has been cooled down to perform humidity detection with high accuracy.

The humidity detector of the invention will be further described with reference to the time charts of FIG. 10. The time circuit 13 is made up of a pulse generator (NE 555, for instance), with a pulse period of the order of five seconds, a binary counter (TC4020BP, for instance) and a shift register (TC4015BP for instance) so as to output signals in five seconds, one minute and ten minutes, and in twenty-four hours. At twenty-four hours, a signal is applied to the reset terminals of the pulse oscillator, the binary counter and the shift register to reset all of them. Under this condition, the measurement is performed for five seconds. Thereafter, the cleaning operation (one minute) and the output holding operation (ten minutes) are carried out, and then the humidity measurement is performed repeatedly over twenty-four hours. The above-described operations are as indicated in the time charts of FIG. 10. Any timer circuit can be employed as the timer circuit 13 if it permits the humidity detecting circuit 11 to perform its operations according to the above-described operating time charts of FIG. 10. As was described above, the cleaning operation is started after the measurement has been performed for five seconds. The reason for this is that the period of time for measurement should be longer than one second to allow the stable operation of the humidity detecting circuit 11.

Figure 11:
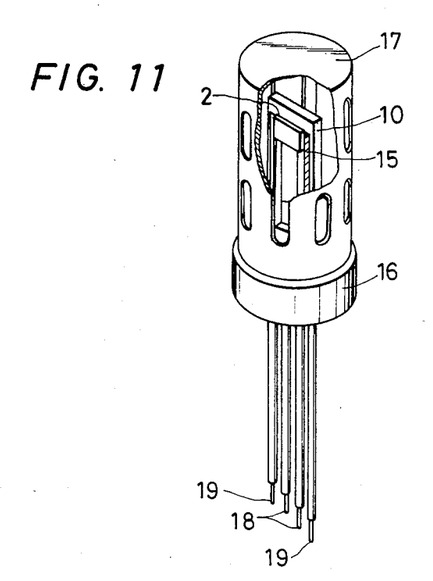
FIG. 11 is a perspective view showing a ceramic humidity sensor in the humidity detector according to the invention.

FIG. 11 is a perspective view showing one example of the ceramic humidity sensor 2 employed in the humidity detector according to the invention. As shown in FIG. 11, the humidity sensor 2 is fixedly attached to a ruthenium electrode 15 on the ceramic heater 10, composed of alumina or the like. These components are supported on a base 16 of silicone rubber or the like, and sealed into a stainless steel cover 17. Further shown in FIG. 11 are sensor lead wires 18 and heater lead wires 19.

The materials and advantages of the metal oxide ceramic humidity sensor have previously been discussed.

The humidity detector according to this aspect of the invention provides no abnormal output when it is started again, for instance, after it is stopped momentarily or after the stoppage of electric supply. Therefore, the humidity detector of the invention can be employed, with high reliability, for control of an air conditioning system. Thus, the humidity detector of the invention should be highly appreciated in its industrial application.

It may be considered to provide a buffer battery in the conventional circuit. However, if the buffer battery is employed in this manner, then the humidity detecting circuit becomes intricate in construction and high in manufacturing cost. On the other hand, the humidity detector provided according to the invention is low in manufacturing cost and has a high accuracy. That is, it is more practical in use.

In the case where the operating period of time of a system using the humidity detector of the invention is shorter than twenty-four hours, and the power switch is turned off before the ceramic humidity sensor cleaning time (24 hours) and turned on again for humidity measurement, the humidity detector of the invention can measure the humidity of the atmosphere under test before the lapse of ten minutes. That is, the humidity detector of the invention has an excellent instantaneous starting characteristic and can be readily handled. This invention should be highly appreciated in this point also.

Turning now to the third aspect of the invention, in one example of the conventional humidity detector cleaning method, immediately when the power switch is turned on, the timer circuit is operated and the heat cleaning operation is effected, and in a predetermined period of time the heat cleaning operation is performed again, and thereafter is repeatedly carried out. In one of the above described embodiments of the invention, the heat cleaning operation is started a predetermined period of time (1 to 5 seconds) after the power switch is turned .on. Thereafter, the cleaning operation is repeatedly carried out, for instance, at a period of 24 hours. The above-described humidity detector is modified according to the third aspect of the invention in such a manner that the circuitry is maintained unchanged and is connected to an external power source when necessary. As a result, upon connection of the external power source, the timer circuit is reset with the same effect as though the power switch is turned on again. That is, the cleaning operation is repeatedly carried out a predetermined period of time after application of the external input similarly as in the other humidity detectors.

This third aspect of the invention covers a humidity detector in which the external input is supplied to the timer circuit in a single line system instead of a two-line system, which contributes to simplification of the modification.

According to the invention, the heat cleaning of the humidity sensor can be achieved at a desired time by adding a simple circuit. Therefore, in the atmosphere contaminated much more than usual, the humidity can be measured with high accuracy. Thus, the invention can provide a humidity detector which is increased in the degree of freedom in operation such as synchronization with the humidity measuring system. That is, the humidity detector of the invention can be operated with ease.

Figure 12:
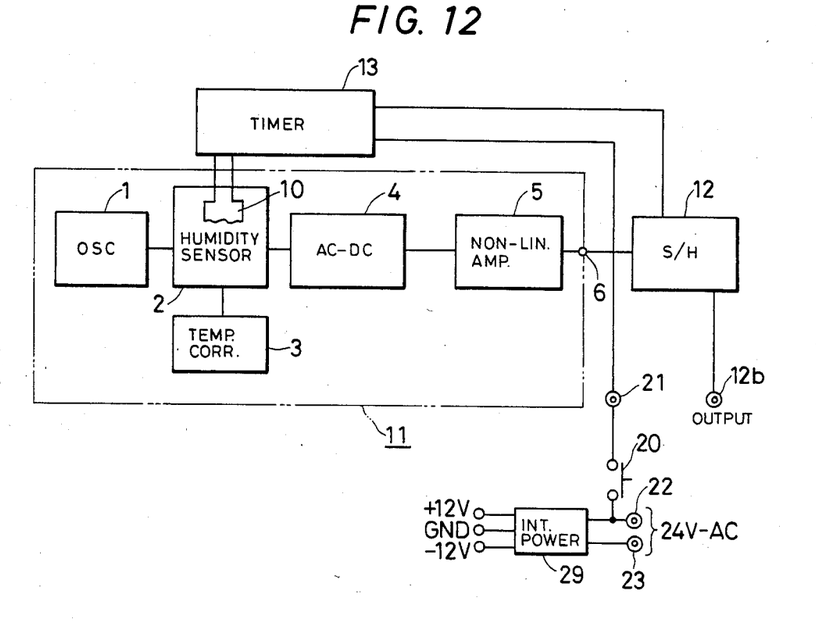
FIG. 12 is a block diagram of a humidity detector according the third aspect to this invention.
Figure 13:
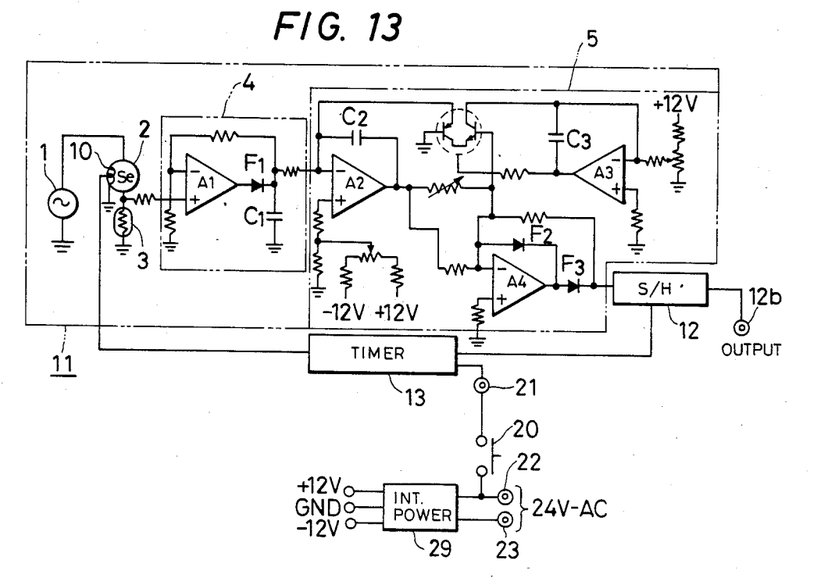
FIG. 13 is a circuit diagram showing a concrete example of the humidity detector of FIG. 12.

One example of a humidity detector according to this third aspect of the invention will be described with reference to the accompanying drawings FIG. 12 is a block diagram showing the humidity detector of the invention, and FIG. 13 is a circuit diagram, partly as a block diagram, showing the humidity detector in more detail.

The humidity detector of FIG. 12 is similar to that of FIG. 7. However, the specific feature of the third aspect of the invention resides in that the output terminal 6 of the humidity detecting circuit 11 is connected to the sample and hold circuit 12. The sample and hold circuit 12 is connected to the timer circuit 13 provided for the ceramic heater 10. One terminal of an input power source at 24 V-AC or an internal power source 29 at +12 V-DC for heat cleaning is connected through a self-return contact switch 20 and an input terminal 21 to the timer circuit 13 so that an external input is applied to the timer circuit 13 at a desired time and heat cleaning is carried out at that desired time. In FIGS. 12 and 13, the external input 21 is obtained through one of the terminals 22 and 23 of the input power source at 24 V-AC.

In the specific example of the humidity detector shown in FIG. 13 a thermistor is employed as the temperature correcting element of the ceramic humidity sensor 2, and a logarithmic amplifier circuit is used as the non-linear amplifier circuit 7. The AC power source, namely, the oscillator 1 is connected to the ceramic humidity sensor 2. A constant voltage is applied to the series circuit of the variable resistance of the humidity sensor 2 and the thermistor 3. The so-divided voltage is amplified and rectified by the AC-DC conversion circuit 4 to obtain a DC output. The DC output is subjected to logarithmic amplification by amplifiers $A_2$ and $A_3$ and a pair of transistors Tr in the logarithmic amplifier circuit 7 so as to be made linear to thereby obtain a voltage output of 10 mV/% RH (relative humidity).

According to the invention, the sample and hold circuit 12 is connected to the output terminal 6 of the humidity detecting circuit 11, to hold the output. The sample and hold circuit 12 is further connected to the timer circuit 13 provided for the ceramic heater 4. The timer circuit 13 performs the dual functions. The first function is to energize the heater at the latest at one to five seconds after the starting of the humidity detecting circuit and to keep it energized for about one (1) minute. The second function is to maintain the output held in the sample and hold circuit 12 for about ten (10) minutes including about nine (9) minutes required for cooling down the humidity sensor 3. Thereafter the sample and hold circuit 12 is released, and the output 6 of the humidity detecting circuit 11 is delivered out.

Immediately when a power switch (not shown) is turned on, the heater 10 is energized, i.e., heated to burn foreign matter on the surface of the ceramic humidity sensor 2 to thereby remove them therefrom. This operation is called "a cleaning operation". In the above described second embodiment, during heat cleaning, the humidity sensor 2 has such a high temperature that the output cannot be reliably detected. Therefore the output provided when the humidity sensor 2 has a low temperature before the heat cleaning is thereafter held. In this method, with the input value being not stable at all, the output is held. However, the held humidity detection value is low in accuracy.

In order to eliminate the above-described difficulty accompanying this method, in the humidity detector of third aspect of the invention, with the aid of the timer circuit 13 the cleaning heater 10 is activated only after one to five seconds after the power switch is turned on. A first signal is applied from the timer circuit 13 to the humidity detecting circuit 7 in order to operate it. After the humidity output 6 provided by the humidity detecting circuit 11 is applied to the sample and hold circuit 12, the cleaning heater 10 starts to heat the humidity sensor 2. As a result, foreign matter on the surface of the humidity sensor 2 is burnt or vaporized. That is, the foreign matter is removed from the humidity sensor 2. Thus, the automatic cleaning operation is accomplished.

Figure 14:
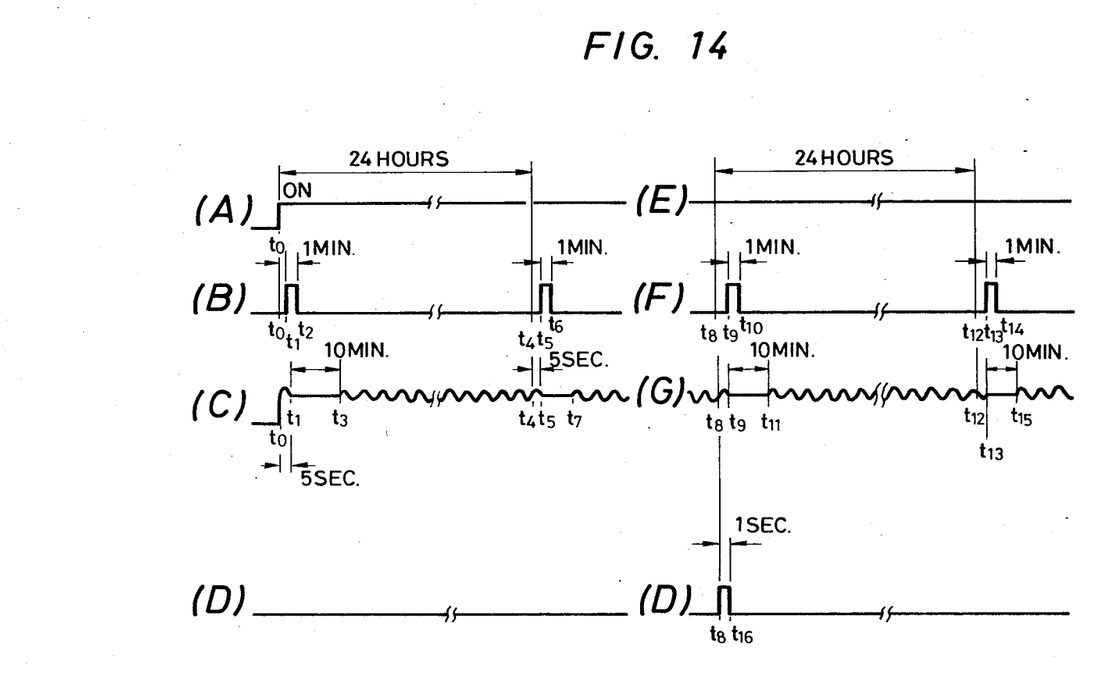

FIG. 14 shows the time chart of the automatic cleaning operation and the time chart of the forced cleaning operation which is obtained by providing the reset contact means according to the invention.

As shown in trace (A) of FIG. 14, upon application of the input power source of 24 V-AC (at the time instant $t_0$) the humidity detector becomes ready for humidity measurement. This operation corresponds to one to five seconds, $t_0$ to $t_1$ indicated in trace (C) of FIG. 14. As shown in trace (B) of FIG. 14, the heater 10 is energized at the time instant $t_1$ and deenergized at the time instant $t_2$. The time of energization, $t_1$ to $t_2$, is about one minute. The humidity sensor 2 is heated by the energization of the heater 10, and the temperature of the humidity sensor 2 is thereby increased, as a result of which it is impossible to perform the measurement. Accordingly, the humidity measuring circuit 11 is effectively not operated during the nine minutes which are required to cool down the humidity sensor 2 after its deenergization. That is, energizing the heater 10 of the humidity sensor 2 is started at the time instant $t_1$. The heater is deenergized at the time instant $t_2$ and after the sensor has been cooled down, the humidity output is provided at the output terminal 12b at the time instant $t_3$. Therefore, the humidity measuring circuit must be started over a period of ten minutes, $t_1$ to $t_3$. As shown in trace (B) of FIG. 14, at the time instant $t_4$, 24 hours after the application of the power source at the time instant $t_0$, the reset signal is supplied to the timer circuit 13. Then, the measurement is carried out for five (5) seconds (ending at the time instant $t_5$). The heater is energized for one minute from $t_5$ to $t_6$. When the humidity sensor 2 is heated with the heater 10 energized again, the output 12b is held at the state before the heater 10 was energized by the sample and hold circuit for ten minutes ($t_5$ to $t_7$). After the time instant $t_7$ the ordinary, real-time humidity measurement is performed. The automatic cleaning operation as described above is repeatedly carried out.

If the atmosphere around the humidity sensor 2 is contaminated much more than usual, it is necessary to perform an optional cleaning operation for instance every twelve hours in addition to the automatic cleaning operation which is carried out repeatedly every twenty-four hours. In the conventional method, the reset operation cannot be performed without disconnecting the power source for the humidity detector. On the other hand, in the method of the invention, one terminal of the input power source 24 V-AC, which can be applied at a desired time, or a terminal +12 V of the internal power source 29 is connected through the self-return contact switch 20 to the timer circuit 13 to reset the timer circuit 13. Five seconds after this switching operation, the heater 10 is energized for one minute while the output, provided by the humidity detecting circuit 11 before the heat cleaning operation, is held by the sample and hold circuit 12 for ten (10) minute ($t_9$ to $t_{11}$). At the time instant $t_{11}$, the humidity sensor 2 has been cooled down. Thus, the forced cleaning operation through the resetting of the timer circuit has been accomplished, and the ordinary humidity measurement can be made again.

The forced cleaning operation has been accomplished as described above. Five (5) seconds after the time instant $t_{12}$, itself twenty-four hours after the reset start time instant $t_8$, the heater 10 is again energized by the operation of the timer circuit 13, so that the cleaning operation is carried out according to the ordinary automatic cleaning cycle Thereafter, the above-described operations are repeatedly carried out. As shown in trace (D), the contact closure time of the self-return contact switch 11 permitting a cleaning operation at a desired time is within one second ($t_8$ to $t_{16}$).

Figure 15:
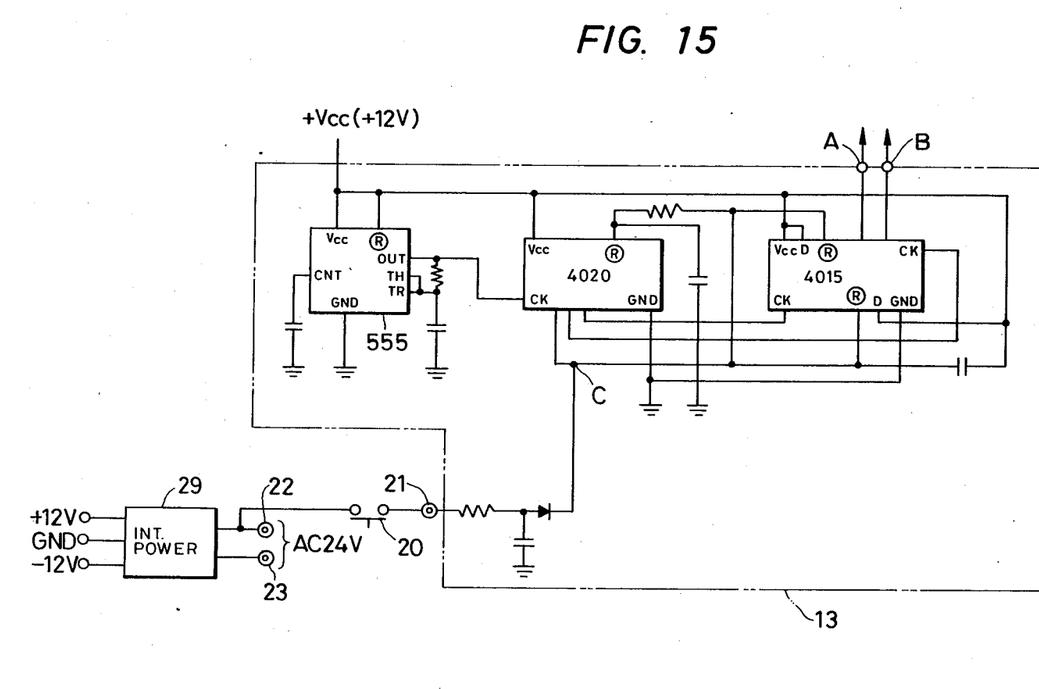
FIG. 15 is a circuit diagram showing one example of a timer circuit of FIG. 13 in more detail.

FIG. 15 is a circuit diagram showing one example of the connection of the timer circuit and the optional cleaning operation circuit of FIG. 13 in more detail. In FIG. 15, an output terminal A carries the signal provided in one minute. Another output terminal B carries the signal provided in ten minutes. An output terminal C carries the periodic timer signal provided every twenty-four hours. In the circuit of FIG. 15, one hot terminal 22 of the input power source 24 V-AC which is used to perform the cleaning operation at a desired time is connected, in a single line system, through the self-return contact switch 11 to the output terminal C provided for the automatic cleaning operation which is carried out every 24 hours. As a result, the power source can be connected to the timer circuit at any desired time. Therefore, even when the automatic cleaning signal to be provided every 24 hours is not provided at the output terminal, the optional cleaning signal can be applied to the terminal C. That is, the optional cleaning operation can be performed with the external input. In this connection, it goes without saying that a two-line system may be employed in such a manner that the +12 V terminal of the internal power source 10 is additionally connected through the self-return contact switch 11 to the external input terminal 13 at a desired time.

As is apparent from the above description, the conventional humidity detector with the automatic cleaning circuit is slightly modified or provided with the additional circuit according to the invention so that the optional cleaning external input can be applied to the humidity detector when necessary. Therefore, the hot cleaning of the humidity detector can be started by applying the optional cleaning external input at a desired time. Accordingly, the humidity detector according to the invention is effective, especially in the case where, in addition to the automatic cleaning operation which is carried out every twenty-four hours, the temporary cleaning operation should be frequently carried out because the humidity detector is used under undesirable conditions. For instance, the environmental atmosphere is contaminated much more than usual. Furthermore, the humidity detector of the invention can be readily synchronized with the automatic cleaning system, i.e., the operability thereof has been significantly improved. Thus, the humidity detector of the invention should be highly effective in industrial use.

What is claimed is:

1. A humidity detecting circuit comprising:
a humidity sensor providing an AC output;
an AC-DC conversion amplifier circuit receiving said AC output of said humidity sensor and providing a DC output;
a non-linear amplifier circuit receiving said DC output of said AC-DC conversion amplifier circuit and providing a signal indicating a relative humidity;
wherein said humidity sensor is a ceramic humidity sensor and further comprising a heater for selectively heating said humidity sensor to remove impurities on a surface thereof;
an output holding circuit receiving said signal indicating a relative humidity;
a timer circuit controlling a turning on of said heater and said output holding circuit after a set period, whereby said output holding circuit holds said signal indicating said relative humidity while said heater is operating; and
external means for selectively resetting said timer circuit, said resetting means including an external input terminal.

2. A humidity detecting circuit as recited in claim 1, wherein said resetting means comprises only one said external input terminal.

3. A humidity detecting circuit as recited in claim 2 wherein said one external input terminal is connected to a power source of said humidity detecting circuit through a switching means.

4. A humidity detecting circuit comprising:
a humidity sensor providing an AC output;
an AC-DC conversion amplifier circuit receiving said AC output of said humidity sensor and providing a DC output;
a non-linear amplifier circuit receiving said DC output of said AC-DC conversion amplifier circuit and providing a signal indicating a relative humidity;
wherein said humidity sensor is a ceramic humidity sensor and further comprising a heater for selectively heating said humidity sensor to remove impurities on a surface thereof;
an output holding circuit receiving said signal indicating a relative humidity;
a timer circuit controlling a turning on of said heater and said output holding circuit after a set period, whereby said output holding circuit holds said signal indicating said relative humidity while said heater is operating; and
wherein after a power-switching starting of said timer circuit, said timer circuit controls said output holding circuit to hold said signal indicating said relative humidity beginning at a time after more than one second following said power-switching starting and thereafter controls said heater to heat said humidity sensor.

5. A humidity detecting circuit as recited in claim 4, wherein said timer circuit periodically following said power-switching starting both controls said output holding circuit to hold said signal indicating said relative humidity and thereafter controls said heater to heat said humidity sensor.

6. A dew point detecting circuit comprising:
a humidity sensor providing an AC output;
an AC-DC conversion amplifier circuit receiving said AC output of said humidity sensor and providing a DC output;
a on-linear amplifier circuit receiving said DC output of said AC-DC conversion amplifier circuit and providing a signal indicating a first dew point at a predetermined temperature;
first temperature correcting means for modifying a temperature dependence of said humidity sensor as a function of temperature;
wherein said signal indicating said first dew point is an analog signal and further comprising:
means for measuring a temperature; and
analog temperature correcting means receiving said analog signal indicating said first dew point and an output of said temperature measuring means and providing an analog output indicating a dew point.

7. A dew point detecting circuit as recited in claim 6, wherein said signal indicating said relative humidity indicates a second dew point at a predetermined temperature.

8. A dew point detecting circuit as recited in claim 6, wherein said analog correcting means linearly combines said analog signal indicating said first dew point and said output of said temperature measuring means.

* * * * *